United States Patent [19]

Hayhurst et al.

[11] Patent Number: 5,269,809
[45] Date of Patent: Dec. 14, 1993

[54] LOCKING MECHANISM FOR USE WITH A SLOTTED SUTURE ANCHOR

[75] Inventors: John O. Hayhurst, Milwaukie, Oreg.; Alan A. Small, Needham; Jeffrey C. Cerier, Franklin, both of Mass.

[73] Assignee: American Cyanamid Company, Wayne, N.J.

[21] Appl. No.: 681,129

[22] Filed: Apr. 5, 1991

Related U.S. Application Data

[63] Continuation-in-part of Ser. No. 548,383, Jul. 2, 1990.

[51] Int. Cl.⁵ .............................................. A61B 17/00
[52] U.S. Cl. .................... 606/232; 606/220; 606/151
[58] Field of Search ............... 606/72, 144, 145, 220, 606/151, 232; 411/508, 509, 510, 512; 24/136, 543

[56] References Cited

U.S. PATENT DOCUMENTS

| | | | |
|---|---|---|---|
| 3,664,345 | 5/1923 | Dabbs et al. | 128/335 |
| 3,745,772 | 11/1974 | Smith | 128/335 |
| 3,910,281 | 10/1975 | Kletschka | 128/335 |
| 3,976,079 | 8/1976 | Samuels et al. | 128/335 |
| 4,235,238 | 11/1980 | Ogiu et al. | 606/145 |
| 4,532,926 | 8/1985 | O'Holla | 606/232 |
| 4,669,473 | 6/1987 | Richards et al. | 606/220 |
| 4,688,561 | 8/1987 | Reese | 128/92 |
| 4,705,040 | 11/1987 | Mueller et al. | 128/334 |
| 4,741,330 | 5/1988 | Hayhurst | 606/86 |
| 4,750,492 | 6/1988 | Jacobs | 128/335 |
| 4,898,156 | 2/1990 | Gatturna et al. | 606/232 |
| 5,046,513 | 9/1991 | Gatturna et al. | 606/232 |
| 5,078,731 | 1/1992 | Hayhurst | 606/232 |
| 5,100,417 | 3/1992 | Cerier et al. | 606/232 |

Primary Examiner—Stephen C. Pellegrino
Assistant Examiner—Gary Jackson
Attorney, Agent, or Firm—Douglas E. Denninger

[57] ABSTRACT

A locking mechanism having a locking element carried by one or more strands of suture material. One end of the suture is attachable to an anchor having a slot extending from a trailing end of the anchor toward a leading end. A portion of the suture is at least partially disposable in the slot. A separate locking member engages the locking element to secure tissue relative to the anchor.

37 Claims, 3 Drawing Sheets

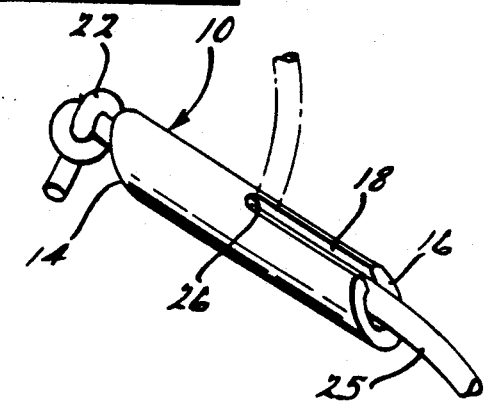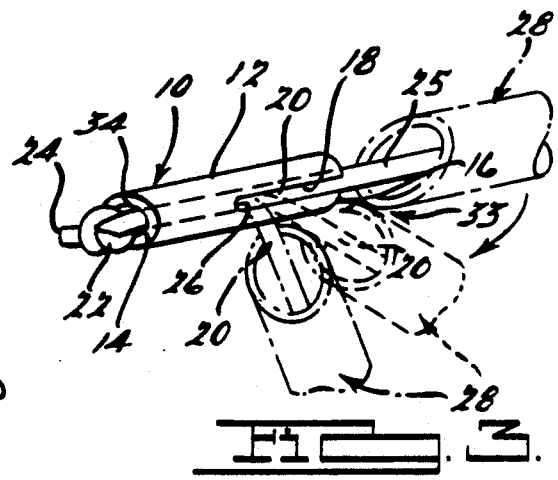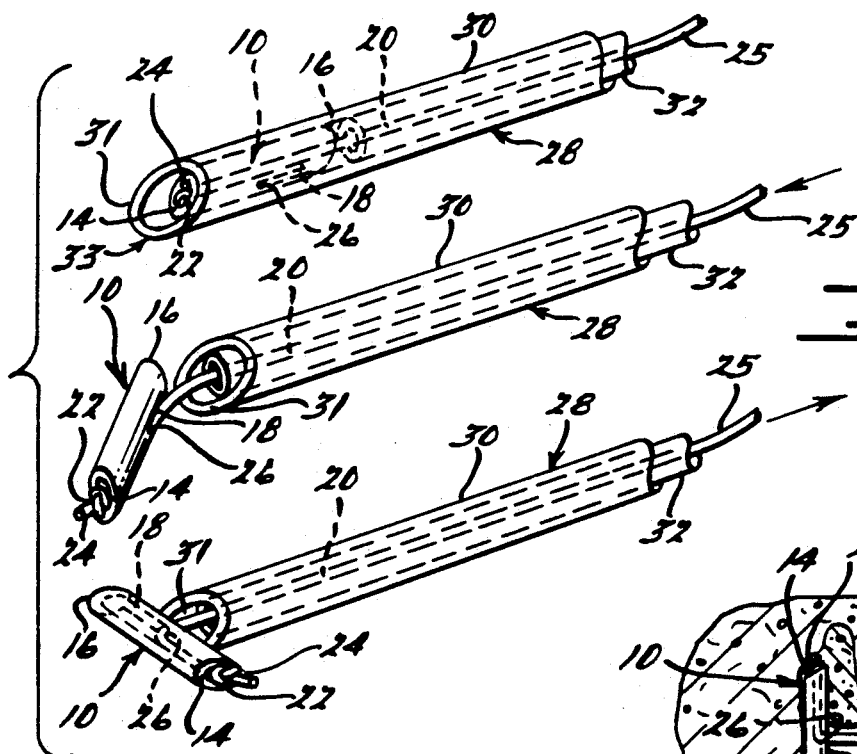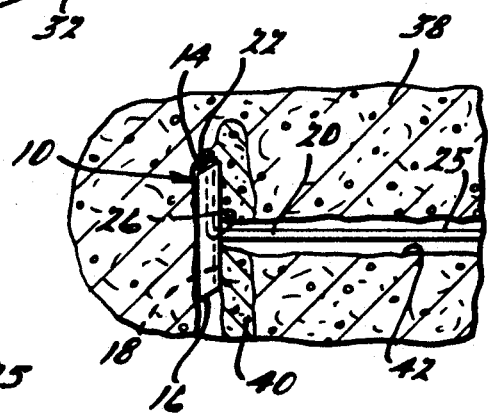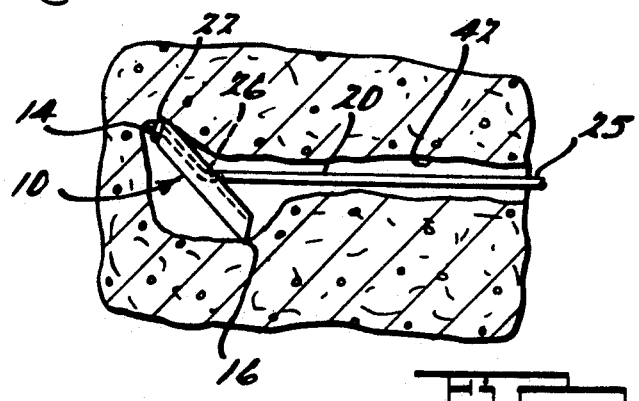

LOCKING MECHANISM FOR USE WITH A SLOTTED SUTURE ANCHOR

CROSS REFERENCE TO RELATED APPLICATIONS

This is a continuation-in-part of commonly-owned U.S. patent application Ser. No. 548,383, filed on Jul. 2, 1990.

TECHNICAL FIELD

The present invention relates to anchors for surgical sutures and more particularly relates to small elongated structures which are attached to a suture and which are inserted lengthwise through a hole in body tissue and deployed by rotating the structure generally transverse to the suture after insertion. The suture anchors can be used to firmly hold together two or more pieces of body tissue for reattachment.

BACKGROUND ART

Suture anchors have been developed for anchoring sutures during arthroscopic surgery with single side access. Such suture anchors are generally inserted with special tools for placement of the suture anchor and manipulation from one side of the body part after insertion.

One example of such a suture anchoring device is disclosed in U.S. Pat. No. 4,669,473 to Richards, et al. which is assigned to the assignee of the present invention. The Richards patent discloses a surgical fastener having a head portion and a filament portion normally arranged in a "T-shaped" configuration. The head portion has at least one pointed end so that when the head portion is implanted in body tissue, the head portion will attach itself securely to the body tissue. The surgical fastener is inserted by a tool including a hollow sheath through which the head of the T-shaped fastener is forced into position by a ram. The filament connected to the head is pulled with the head through a slot in the sheath. The resiliency of the fastener causes it to return to its normal T-shaped configuration with the head disposed generally transverse or at an acute angle to the filament. In this orientation, the pointed ends of the fastener head lodge themselves into the surrounding tissue. The tool is then removed leaving the free end of the filament extending from the tissue for subsequent use by the surgeon.

Another approach to providing a suture anchor intended to be anchored behind cartilage is disclosed in U.S. Pat. No. 4,741,330 to Hayhurst. The Hayhurst suture anchor also has a T-shaped configuration and is deployed for implantation with the ends of the head doubled over and pointing away from the filament. After insertion, the ends of the head due to their natural resiliency tend to return to their normal perpendicular orientation relative to the filament. Alternatively, the T-shaped anchor may be deployed with the filament folded over parallel to the head and forced into position through an elongated tubular insertion tool.

While the above surgical fasteners have proven to be dependable and effective, several disadvantages have been encountered which are addressed by the present invention. For example, the diameter of the opening in the body or tissue required for insertion in each of the above references must be greater than the combined diameter of the head of the T-shaped anchor and the filament. Also, the Richards' anchor is molded in one piece and includes a molded filament which may be more difficult to tie off than a conventional suture. With the Hayhurst anchor, joining the suture material to the plastic anchor sometimes involves intricate manufacturing and quality control procedures.

For arthroscopic procedures, the small space available to operate limits the size of instruments which can be used. Generally if such instruments are made smaller, they are more practical and can be used more efficiently and easily. Similarly, the smaller the hole required for insertion of the surgical instruments, the less trauma is caused to the patient by the operation and the less time it takes for the surgical site to heal.

The suture anchor and suture of the present invention, when installed according to the method of the present invention minimizes these and other problems.

Accordingly, it is a principal object of the present invention to provide an improved single-sided surgical suture fastener which minimizes the diameter of the insertion opening. Another object is to provide an improved surgical suture fastener which is simple and inexpensive to make.

A further object of the present invention is to provide an improved T-shaped suture anchor and a method of constructing it. Still another object is to provide an improved method for deploying a T-shaped surgical suture fastener.

Another object of the present invention is to provide an improved T-shaped suture anchor which has a stronger connection between the suture and the anchor and utilizes the full strength of the suture.

An additional object of the invention is to provide a T-shaped surgical suture fastener which has stop means on the suture for mating with a locking member and thereby being able to securely hold together pieces of tissue.

DISCLOSURE OF THE INVENTION

These and other objects of the invention are achieved by a novel suture anchor and suture as described below. A suture anchor and suture in combination are provided comprising a suture and an elongated tubular anchor having a slot extending part way from the trailing end toward the leading end. The suture is knotted or otherwise affixed adjacent its terminal end with the knot engaging the leading end of the anchor. The suture is threaded axially through the anchor from the leading end to the trailing end forming a thin elongated package for insertion. The suture shifts along the slot during deployment to a position wherein the suture extends from an intermediate point on the anchor to form a generally T-shaped surgical suture fastener.

According to another aspect of the present invention, a suture anchor for anchoring a suture to tissue comprises an elongated tube having a leading end and a trailing end. The tube has a slot extending linearly from the trailing end of the tube preferably approximately halfway to the leading end of the tube.

The suture is secured to the leading end of the tube. The anchor is rotatable between a first position in which the suture extends completely through the tube and a second position in which the suture extends from the leading end of the tube and exits from the slot.

According to another aspect of the present invention, the ends of the tubular member preferably define leading and trailing ends disposed at oblique angles to the central axis of the tube. The leading end defines a pointed structure which aides in insertion. The oblique angulation of the trailing end assists in rotating the suture anchor to its toggle position forming a T-shaped anchoring structure.

The slot extends linearly from the trailing end of the head and preferably starts at the axial inboard most point of the trailing end (i.e. the point of the trailing end which is closest to the mid-point of the anchor).

The suture anchor and suture may be assembled prior to delivery to the operating room or may be assembled by the surgeon prior to insertion in a patient.

According to the method of making a suture anchor according to the present invention, a T-shaped anchor is formed using a small elongated tubular member having leading and trailing ends. A slot is formed in the tubular member extending from the trailing end to an intermediate point between the two ends. A suture is secured to the leading end of the tubular member and threaded through the tubular member to the trailing end.

The method of deploying the suture anchor comprises the steps of inserting the anchor using a hollow tool with the first end of the anchor being initially inserted by the tool into (or through) the body tissue to a desired depth, generally behind cartilage. As inserted, the suture, which is secured to the first end of the tubular member, extends the length of the anchor. After the anchor is pushed through the end of the tool, tension is applied to the suture causing the anchor to grip the tissue and rotate to a toggle position with the suture being pulled through the slot.

The suture anchor of the present invention can also be used with a suture locking means on the suture to securely hold together two or more pieces of body tissue.

BRIEF DESCRIPTION OF DRAWINGS

FIG. 1 is an elevational view of the suture anchor of the present invention;

FIG. 2 is a perspective view of the suture anchor, suture and a fragmentary view of the installation tool showing the suture anchor as initially inserted, as partially inserted, and as finally in its toggle position;

FIG. 3 is a perspective view of the suture anchor illustrating an enlarged view of the inserting and toggle procedures;

FIG. 4 is a cross-sectional view showing the suture anchor and suture with the anchor inserted behind a section of cartilage;

FIG. 5 is a cross-sectional view showing the suture anchor and suture inserted in soft tissue;

BEST MODE(S) FOR CARRYING OUT THE INVENTION

Figure 6:
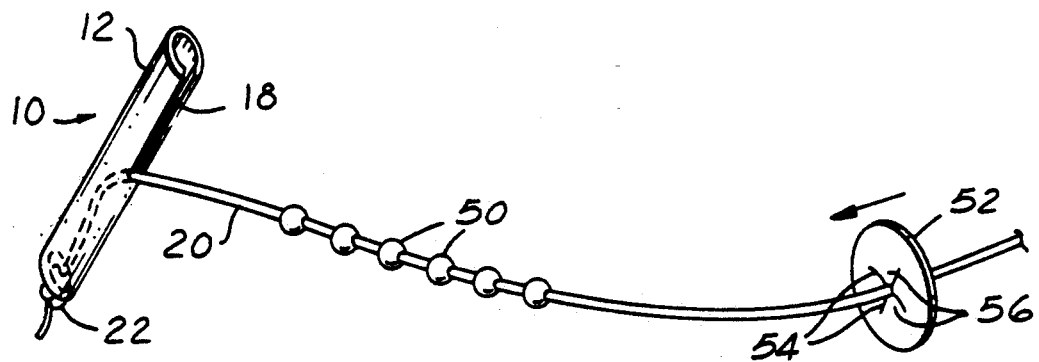
FIG. 6 illustrates one use of the present inventive suture anchor with a suture having locking means thereon.

Referring now to FIG. 1, the anchor 10 of the present invention is shown. The anchor 10 is formed as a tube 12 having a leading end 14 and a trailing end 16 at opposite ends of the tube 12. A slot 18 extends from the trailing end 16 to a point intermediate the leading end 14 and the trailing end 16. The slot 18 preferably extends to the approximate midpoint of the tube 12.

The ends 14 and 16 of the suture anchor are angled as shown. The leading end 14 is angled to allow point 15 to aid in the insertion of the anchor through the body tissue. The trailing edge 16 is angled to aid in rotating the anchor once it is placed in position and to help lead and place the suture into the slot 18. The edge 17 which is the axial outboard most point of the anchor trailing end (i.e. the end of the anchor further from its mid-point) is adapted to grab or dig into the tissue thereby allowing tension on the suture to cause the anchor to toggle or rotate into a T-shaped configuration. The slot 18 is preferably positioned such that it opens at the axial inboard most point 19 of the anchor (i.e. the edge of the slanted end 16 which is closest to the mid-point of the anchor). This allows the slanted end 16 to direct the suture towards and into the slot 18 when the anchor is rotated.

Although it is preferred that the slot 18 extend approximately one-half of the length of the tube 12 (in order to provide substantially equal or equivalent anchoring surfaces on opposite sides of the suture), it is possible within the scope of the present invention for the slot to extend less than or more than such distance, so long as it operates in an equivalent manner and provides sufficient anchoring effects. Of course, extending the slot too far towards the leading end may weaken the tube in an unsatisfactory manner, and not extending the slot a sufficient length may prevent the tube from rotating into a satisfactory anchoring position.

Referring to FIGS. 2 and 3, the anchor 10 is shown with a suture 20 positioned in it. In FIG. 3, the suture 20 as shown in solid lines in an insertion position, and in phantom lines in its partially inserted position and in its deployed or toggle position in solid lines. The suture 20 is attached to the anchor 10 by means of a knot 22. The knot 22 is large enough to prevent slippage of the suture 20 through the tube 12. The knot 22 is formed on the terminal end 24 of the suture 20.

It is understood that other means for securing the suture to the anchor 10 are possible including heat staking, gluing, ultrasonic welding, pinning or other similar means of locking the suture 20 to the anchor 10.

Referring to FIG. 2, insertion of the anchor 10 and suture 20 is illustrated in three phases. Insertion of the anchor is performed a cannulated insertion tool 28 (shown fragmentarily). Upon initial insertion, the anchor 10 and suture 20 are confined within a hollow outer needle 30 of the insertion tool 28. The suture 20 extends from the knot 22 formed at the leading end 14 of the tube 12 through the trailing end 16 of the tube. The suture then extends through the pusher tube 32 which is concentrically located within the outer needle 30. Insertion continues as shown in FIG. 2 to a mid-insertion phase wherein the anchor 10 is pushed beyond the distal end 31 of the outer needle 30 by the pusher tube 32. The anchor 10 then shifts out of alignment with the insertion tool 28 and begins to tip toward a toggle position generally transverse to the axial direction of the suture. The suture is then pulled through the slot toward the base 26 of the slot by applying tension to the suture 20.

As stated above, preferably the leading end 14 of the tube 12 defines a leading face 34 which is obliquely angled relative to the central axis of the tube 12. A trailing face 36 is preferably formed on the trailing end 16 of the tube 12 and preferably lies in a plane parallel to that of the leading face 34 and also obliquely angled relative to the central axis of the tube 12. The trailing face 36 functions to aide in tipping the anchor 10 toward its toggle position after it is free from the outer needle of the insertion tool 28.

The angular orientation of the leading faces creates relatively sharp edges which facilitates locking the anchor 10 in soft tissue. Alternatively, the leading and trailing faces 34 and 36 could be substantially perpendicular to the axis of the tube 12. In the final insertion step (illustrated in FIGS. 2 and 3), the anchor 10 is in a toggle position relative to the length of the suture 20 with the suture 20 exiting the tube 12 at the base 26 of the slot 18.

The leading face of the outer needle 30 of the insertion tool 28 is preferably slanted as shown in FIGS. 2 and 3. Also the leading edge 33 of the face has a sharpened tip. This structure allows the needle 30 to penetrate the skin and/or be moved into position more easily for installation of the anchor. Also, in order to prevent "coring" of tissue or skin when the tool 28 is utilized, preferably the anchor 10 is positioned in the needle 30 substantially flush with the distal end or leading face during insertion. For this purpose, if desired, the angle of the leading face of the outer needle 30 can be the same as the angle of the leading face 34 of the anchor tube 12.

As an alternate embodiment of the insertion tool 28, a thin solid pusher rod (not shown) can be utilized in place of the hollow pusher tube 32 shown in FIG. 2. Once the anchor and suture 20 are positioned in the hollow outer tube 30, the pusher rod can be inserted in the tube and used to push the anchor into its installation and anchoring positions. The use of a pusher rod eliminates the step of threading the suture through the pusher tube. With the exception of use of a pusher rod for a pusher tube, the remainder of the suture anchor installation procedure is the same.

Referring now to FIG. 4, a preferred use of the anchor 10 of the present invention is shown wherein the anchor is inserted in body tissue 38 and anchored to cartilage 40. Holes 42 and 44 are formed in the body tissue 38 and cartilage 40, respectively, by use of any conventional surgical drilling or hole forming means. When the anchor 10 of the present invention is used to secure a suture to cartilage, the insertion tool is inserted through the holes 42 and 44 until the end 31 passes through the cartilage 40. The anchor 10 is then pushed out of the insertion tool and rotated to its toggle position as previously described relative to FIGS. 2 and 3.

Referring now to FIG. 5, use of the anchor 10 of the present invention is shown in soft body tissue 38. A hole 42 is formed in the soft tissue either by the insertion tool or by a prior incision. The anchor 10 and suture 20 are inserted into the hole 42 through use of the insertion tool and the anchor is shifted by applying tension on the suture 20 after the anchor 10 is free from the distal end 31 of the outer needle 30. The leading and trailing ends 14 and 16 of the anchor 10 shift from an insertion position wherein the leading end is first inserted into the tissue to a position wherein the leading and trailing ends assume an approximately perpendicular or toggle position relative to the length of the suture 20.

As indicated, preferably the suture anchor is used to affix a suture to body tissue, generally behind cartilage although it can also be used to affix a suture in body tissue alone. In addition, the suture anchor can be passed entirely through body tissue or cartilage and be positioned on the opposite side outside the body or where body tissue is not present. The installation and operation of the invention will be the same.

The anchor 10 may be made of either a bio-absorbable material or a non-absorbable permanent material. Preferred absorbable materials include polyglycolic acid, polylactic acid or trimethylene carbonate copolymers. Preferred non-absorbable materials include acetal homopolymers or copolymers, polyethylene, polypropylene, polyester and copolymers thereof. The suture material may be any conventional type of suture material, such as Ticron, or Dexon brand sutures which are trademarks of Davis & Geck.

With the present invention, there is not a problem securely affixing the suture to the anchor. The suture does not have to be molded into the anchor which sometimes creates strength problems, but instead utilizes a mechanical fastening system which insures a strong and secure affixation. Also, the bending of the suture at the end of the slot when the anchor is installed in place keeps the full strength of the suture at that point. Fasteners which have a molded head and filament portion often have strength problems caused by the head being bent parallel to the filament during insertion.

FIG. 6 shows an embodiment of the inventive suture anchor 10 used with a locking suture member. The suture anchor has a tubular body 12 with a slot 18 therein. The suture 20 fits through the body and slot and is formed into a knot 22 at one end of the anchor.

A plurality of small spheres 50 are attached to the length of the suture 20 at regular intervals. The spheres are molded onto the suture or formed with it initially. The spheres act as stop members for a locking member such as washer 52. The locking washer 52 has a series of slits 54 that connect at the center of the washer. The slits 54 form a plurality of small flap members 56 which are flexible. The slits and flap members allow the suture 20 to pass through the washer in one direction, but act as a lock or stop and prevent the suture from passing the other way.

Figure 7:
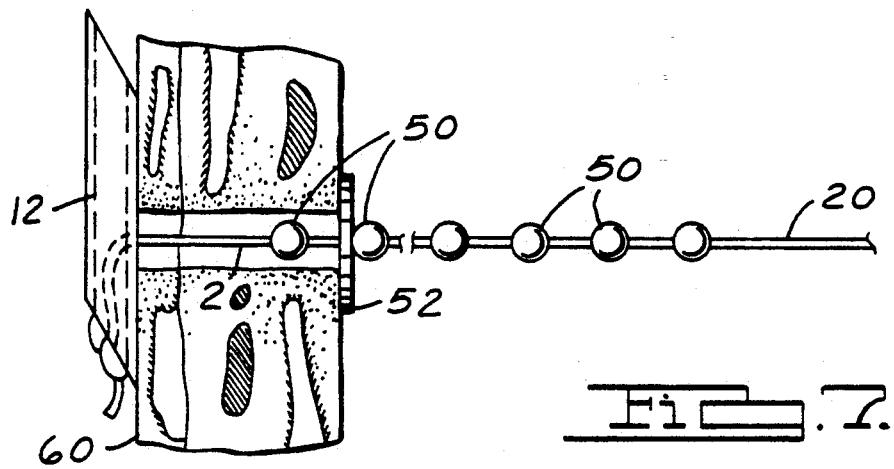
FIG. 7 depicts the use of the invention of FIG. 6 in securely holding together two pieces of body tissue.

When the suture and anchor assembly as shown in FIG. 6 is utilized, the anchor is positioned and set in place as described above and the washer 52 is threaded over the suture and pushed or passed over the spheres 50 until it rests against the body tissue. One use of such an assembly is shown in FIG. 7. The anchor 10 is positioned on one side of tissue 60 and the washer 52 is pushed into position on the opposite side of tissue 62. The excess length of suture 20 with spheres 50 thereon is cut off and discarded. In this manner, tissue pieces 60 and 62 are forced and held securely together until they are reattached or grown together.

Figure 8:
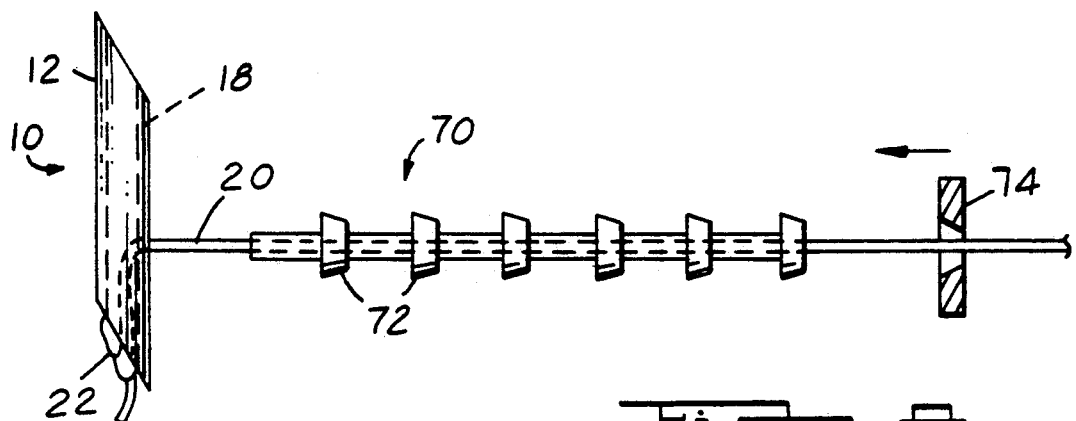
FIG. 8 shows another embodiment of the invention.
Figure 9:
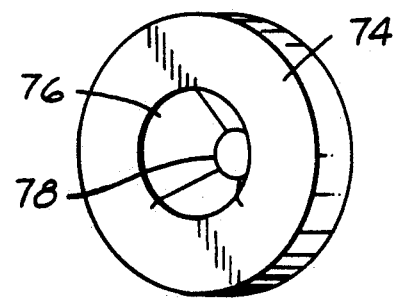
FIG. 9 illustrates a preferred locking washer.

Another embodiment of a suture and slotted anchor assembly is shown in FIG. 8. The suture 20 has an elongated, tubular stop member 70 molded or formed thereon. The member 70 has a series of regularly spaced ribs or ridges 72 thereon. The ribs or ridges 72 act as stops for locking washer member 74, as shown in FIG. 9. The washer 74 has a conical recess 76 in the center divided by a three-slotted passageway 78 for the suture. In use, the assembly shown in FIG. 8 is used in substantially the same manner as the assembly shown in FIGS. 6 and 7.

Figure 10:
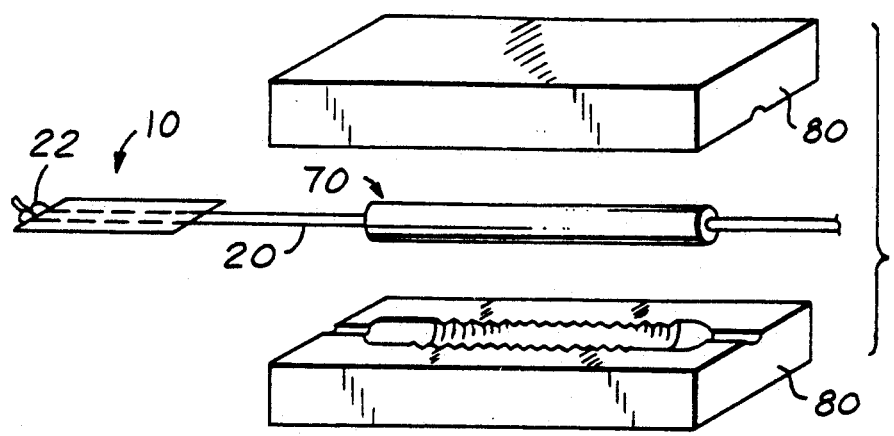
FIG. 10 depicts a method of making one embodiment of the invention.

FIG. 10 shows one method for making the assembly shown in FIG. 8. The suture 20 with anchor 10 at one end has a tubular member 70 placed along its length adjacent the anchor. The suture with the tubular member thereon is then placed in mold 80. The two halves of the mold have a recess therein which forms the ribs or ridges 72 on the tubular member. In order to make the completed assembly, the mold halves are heated and brought together trapping and squeezing the tubular member and suture in between. Heat and pressure from the mold 80 forms the member 70 into the shape shown in FIG. 8 and also securely fastens the member 70 to the suture 20. The forming process alternately could be ultrasonic welding, radio frequency welding, injection molding, compression molding or other similar or conventional methods.

Figure 11:
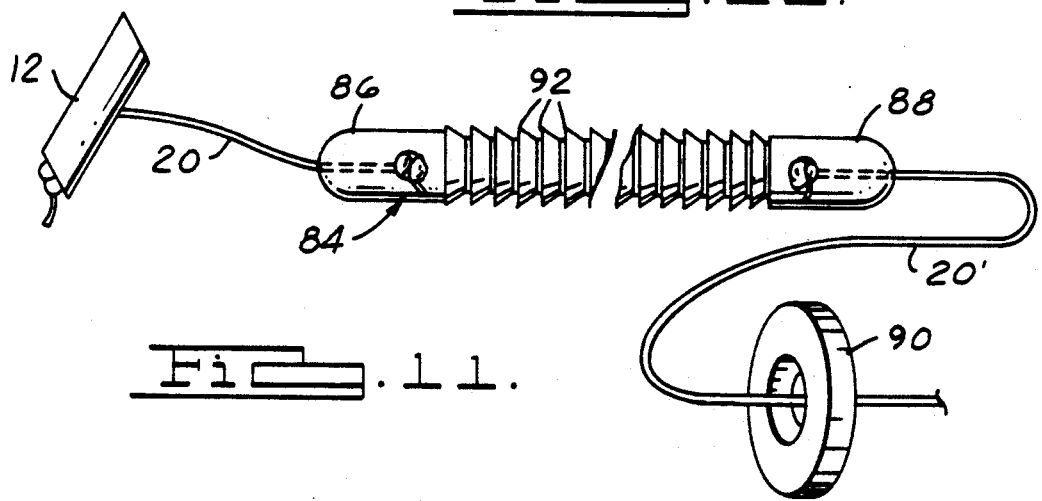
FIG. 11 illustrates still another embodiment of the invention.

FIG. 11 shows still another embodiment of the invention. In this embodiment, a separate and independently molded stop member 84 is attached to the suture 20. The suture 20 is attached (such as by tying) to one end 86 of the member 84. Another suture 20' is attached to the other end 88 of the stop member. A snap-on locking disk or washer 90 is used to mate and lock with the ribs or ridges 92 on the molded stop member 84.

Figure 12A:
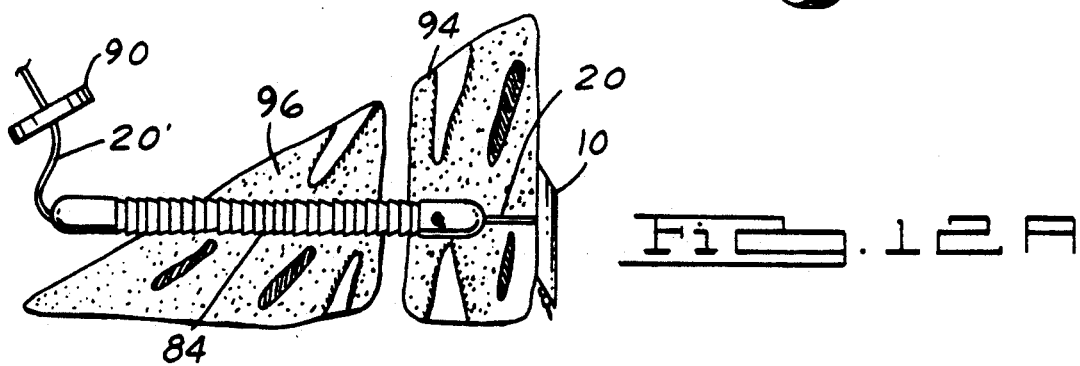
FIGS. 12A and 12B show the use of the invention as set forth in FIG. 11.
Figure 12B:
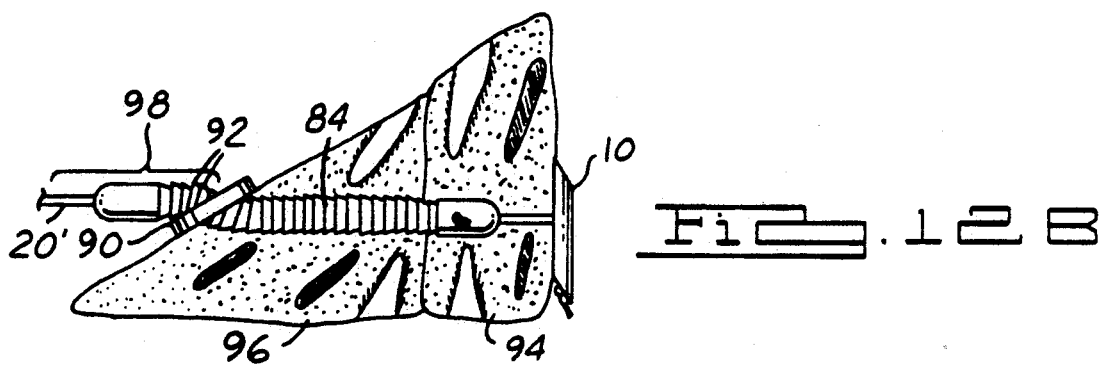

The use of the FIG. 11 embodiment of the invention is shown in FIGS. 12A and 12B. As shown in FIG. 12A, the slotted anchor 10 is inserted and installed in position on one side of two torn or separated pieces of body tissue 94 and 96 and the washer or disk 90 is snapped and slid onto the ribbed stop member 84. The two pieces of tissue are forced together (as shown in FIG. 12B) and held together by the anchors 10 and washer 90. The excess part 98 of the member 84 and the suture 20' are cut off and discarded.

The above-described preferred embodiments are intended to be illustrative of the invention which may be modified within the scope of the appended claims.

I claim:

1. An anchor and a strand of suture material in combination, said anchor comprising a body having a leading end and a trailing end, a slot extending from said trailing end toward said leading end, a portion of said strand being at least partially disposable in said slot, means for attaching said strand of suture material to said leading end of said body with said strand extending from said leading end at least partially through said body, said strand being shiftable between an insertion position in which said strand extends from said body at the trailing end and a toggle position in which said strand extends from said body through said slot, and locking means, carried by said strand, for engaging a separate locking member to secure the locking member relative to said locking means.

2. The combination of claim 1 further including a locking member for cooperating with said locking means to hold said combination together to secure at least two pieces of tissue together.

3. The combination of claim 2 wherein said locking means includes a series of stops disposed on its exterior surface for mating with said locking member.

4. The combination of claim 3 wherein said stops are alternating ridges and depressions.

5. The combination of claim 2 wherein said anchor, said strand, said locking means and said locking member are made from a bioabsorbable material.

6. The combination of claim 1 wherein said body is a tube.

7. The combination of claim 1 wherein said trailing end defines a trailing face disposed at an oblique angle to the central axis of said body.

8. The combination of claim 7 wherein said trailing face is inclined toward said slot.

9. The combination of claim 1 wherein said slot has a width and a depth sufficient to fully accommodate said portion of said strand.

10. A locking element for securing tissue relative to an anchor, comprising an elongated body defining internally means for fastening said body to a first portion of a suture, another portion of the suture being attachable to the anchor, and means, disposed on the exterior of said body, for engaging a separate locking member to secure the locking member relative to said body and thereby secure the tissue between the locking member and the anchor, said means for fastening including a longitudinal passage through which the suture is insertable.

11. The locking element of claim 10 wherein said body is formed of a material which enables it to be compressed onto the suture within said passage to fasten said body to the suture.

12. The locking element of claim 11 wherein said material is capable of sufficient compression to enable said means for engaging to be established on said body after the suture is inserted through said passage.

13. The locking element of claim 12 wherein said means for engaging is establishable on said body as a plurality of ridges formed on said body.

14. The locking element of claim 10 where said means for fastening includes distal means for attaching to the first portion of the suture, and proximal means for attaching to a terminal portion of a second suture.

15. A suture anchor and suture in combination comprising:
a suture;
an elongated anchor;
said suture having a knot tied adjacent a terminal end of said suture and engaging a first end of said anchor;
said anchor having a slot extending from a second end to a slot base intermediate the first and second ends;
said suture being threaded through said anchor from the first end axially through said anchor and through the second end in an insertion position and being shifted through the slot during deployment to a deployed position wherein said suture extends from said anchor at the slot base; and
locking means, carried by said suture, for engaging a separate locking member to secure the locking member relative to said locking means.

16. The combination of claim 15 further including a locking member for cooperating with said locking means to hold said combination together to secure at least two pieces of tissue together.

17. The combination of claim 16 wherein said locking means includes a series of stops disposed on its exterior surface for mating with said locking member.

18. The combination of claim 17 wherein said stops are alternating ridges and depressions.

19. The combination of claim 16 wherein said anchor, said strand, said locking means and said locking member are made from a bioabsorbable material.

20. The combination of claim 15 wherein said body is a tube.

21. The combination of claim 15 wherein said trailing end defines a trailing face disposed at an oblique angle to the central axis of said body.

22. The combination of claim 21 wherein said trailing face is inclined toward said slot.

23. A locking element permanently attachable to a suture comprising an elongated body defining a longitudinal passage through which the suture is insertable and means, disposed on the exterior of said body, for engaging a separate locking member to secure the locking member relative to said body.

24. The locking element of claim 23 wherein said body is formed of a material which enables it to be compressed onto the suture within said passage to fasten said body to the suture.

25. The locking element of claim 23 wherein said body is formed of a material which enables said means for engaging to be established on said body after the suture is inserted through said body.

26. The locking element of claim 25 wherein said means for engaging is a series of alternating depressions and ridges formed on said body.

27. The locking element of claim 23 wherein said means for engaging is a series of alternating depressions and ridges formed on said body.

28. An elongated suture locking element in combination with first and second sections of suture each having proximal and distal portions, the distal portion of the first section being attachable to an anchor member, the locking element comprising an elongated body including a distal end having distal means for attaching to the proximal portion of the first suture section, the proximal suture portion being attached thereto, a proximal end having proximal means for attaching to the distal portion of the second suture section, the distal suture portion being attached thereto, and a center portion having means for engaging a separate locking member.

29. The combination of claim 28 wherein said means for engaging include a plurality of ribs for interlocking with the separate locking member.

30. The combination of claim 28 wherein said distal and proximal means for attaching to said first and second suture sections each include a passage through which the proximal and distal suture portions, respectively, are insertable.

31. The combination of claim 28 wherein said locking element is made from a bioabsorbable material.

32. The locking element of claim 10 wherein said body is permanently attachable to the suture.

33. A suture and locking element in combination comprising:
   a suture; and
   a locking element permanently attached to a portion of said suture and having a longitudinal passage through which said suture extends and means, disposed on an exterior surface of said body, for engaging a separate locking member to secure the locking member relative to said body.

34. The combination of claim 33 in which said means for engaging includes a plurality of stops formed on said body.

35. The combination of claim 34 further including a washer-like element as said separate locking member, said washer-like element defining a passage through which said elongated body is insertable to engage at least one of said stops.

36. The combination of claim 30 wherein said first section passage and said second section passage each communicate with an outer end surface of said distal and proximal ends, respectively, of said locking element.

37. The combination of claim 36 further including a washer-like element as said separate locking member, said washer-like element defining a passage through which said elongated body is insertable to engage at least one of said stops, and said means for engaging includes a plurality of stops for interlocking with said locking member.

* * * * *